(12) United States Patent
Fernfors

(10) Patent No.: US 6,328,725 B2
(45) Date of Patent: Dec. 11, 2001

(54) METHOD OF PRODUCING RECLOSABLE ABSORBENT GARMENTS AND ABSORBENT GARMENTS OBTAINED THEREBY

(75) Inventor: Ingemar Fernfors, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/091,547

(22) PCT Filed: Nov. 26, 1996

(86) PCT No.: PCT/SE96/01537

§ 371 Date: Jun. 22, 1998

§ 102(e) Date: Jun. 22, 1998

(87) PCT Pub. No.: WO97/23180

PCT Pub. Date: Jul. 3, 1997

(30) Foreign Application Priority Data

Dec. 22, 1995 (SE) .................................................. 9504613

(51) Int. Cl.[7] .......................... A61F 13/56; A61F 13/64; A61F 13/15; B32B 31/18
(52) U.S. Cl. ...................... 604/391; 156/461; 156/217; 156/264; 156/266; 156/269; 156/277
(58) Field of Search .......................... 604/391; 156/461, 156/217, 264, 266, 269, 277

(56) References Cited

U.S. PATENT DOCUMENTS

| | | | |
|---|---|---|---|
| 3,629,039 | * 12/1971 | Frick | 156/269 |
| 3,800,796 | * 4/1974 | Jacob | 128/284 |
| 3,847,702 | * 11/1974 | Jones, Sr. | 156/265 |
| 4,309,236 | * 1/1982 | Teed | 156/164 |
| 5,034,007 | * 7/1991 | Igaue et al. | 604/365 |
| 5,147,487 | 9/1992 | Nomura et al. | |
| 5,304,162 | * 4/1994 | Kuen | 604/391 |
| 5,386,595 | * 2/1995 | Kuen | 2/400 |
| 5,545,275 | 8/1996 | Herrin et al. | |
| 5,558,734 | * 9/1996 | Sherrod et al. | 156/164 |
| 5,626,711 | * 5/1997 | Herrmann | 156/496 |
| 5,683,531 | * 11/1997 | Roessler et al. | 156/164 |

FOREIGN PATENT DOCUMENTS

| | | |
|---|---|---|
| 2 254 997 A | 10/1992 | (GB) . |
| WO 95/27461 | 10/1995 | (WO) . |
| WO 95/27462 | 10/1995 | (WO) . |
| WO 95/34266 | 12/1995 | (WO) . |

* cited by examiner

Primary Examiner—Aaron J. Lewis
Assistant Examiner—Michael Bogart
(74) Attorney, Agent, or Firm—Burns, Doane, Swecker & Mathis, L.L.P.

(57) ABSTRACT

The invention relates to a method of producing reclosable absorbent garments, in particular absorbent pants, and to the absorbent garments obtainable by said method. Starting from a continuous web (1) of absorbent articles attached side-by-side and with a line of weakening (6) arranged between adjacent articles, a first strip (8) comprising releasably attachable material is applied across the line (6) at one edge (25) of the web. A second strip of flexible material is also applied across the line (6) at the other edge (26) of the web. The web is then folded longitudinally to form a series of closed, joined adjacent articles. The adjacent articles are then partially separated at said line (6) but without rupturing said strips (8, 13), so as to provide a free zone (15) between said strips (8, 13) and the adjacent separated edges of each article. The strips (8, 13) are then joined together across the free zone (15) to form a plurality of joined garments. The strips (8, 13) may then be severed so as to form individual garments (27) of the reclosable type, or may remain unsevered and be foreseen with a line of weakening for later separation. Due to the particular method and product features of the invention, an in-line process for making closed, reclosable absorbent garments is achieved.

10 Claims, 3 Drawing Sheets

METHOD OF PRODUCING RECLOSABLE ABSORBENT GARMENTS AND ABSORBENT GARMENTS OBTAINED THEREBY

FIELD OF THE INVENTION

The invention relates to a method of producing reclosable absorbent garments. The invention also relates to an absorbent garment as defined in the first part of claim 7, and to a series of closed absorbent garments.

BACKGROUND TO THE INVENTION

Absorbent garments of the reclosable type are known. One such garment is for example a diaper for use by a child or adult incontinent users, said diaper having strips with tabs on one end of said product that can be releasably adhered to a landing zone on the other end of said product when fitted to a baby/child user. One problem with this is however that for putting the garment on, some dexterity is required to grip and position the tab. In older users, such dexterity is often lacking and the garments may be particularly awkward to assemble.

Another type of absorbent product that has been used much in recent years, and which circumvents such problems, is an absorbent garment known generally as a pair of training pants or incontinence pants. The garment is much more convenient and quicker to put on than a reclosable nappy, since it is very similar to a pair of ordinary underpants in that it has a continuous waistband and two leg openings This form allows it to be pulled on like normal pants without any pre-assembly. When the garment becomes soiled however, its removal is problematic. Either the outer clothing has to be removed entirely to take the pants off as normal, which can be difficult in many situations, or the two sides of the pants have to be torn vertically so that the torn garment can be removed between the wearer's legs. The tearing of the side portions in itself can however be difficult, especially again for very old wearers who may lack the strength to tear the product.

A further problem which presents itself is that absorbent pants cannot be adjusted and consequently they may be uncomfortable if exactly the right size is not chosen. Even then, adjustability is desirable to take account of variations in waist size occurring during the day, e.g. after eating. Additionally, a large selection of sizes is required if all body shapes are to be catered for.

Whilst the provision of reclosable fastening arrangements is used to provide adjustability and easy removal in nappies, no totally satisfactory solution has yet been found for applying such a feature to absorbent pants whilst still allowing them to be produced in-line, which is a requirement for economically viable production.

WO-A-95/27462 discloses a method of producing a series of disposable absorbent garments starting from a web of side-by-side open absorbent articles having opposed longitudinal edges with a line of intended separation between said articles. In this method, a first strip of flexible material with a zone of releasably attachable material is placed on the web with the releasably attachable material facing away therefrom. In one embodiment, folding of the garment between its longitudinal side edges is performed. In said embodiment, a second strip of a co-acting releasable material is placed on the opposite side of the web and then the web is then folded between its longitudinal edges so that the co-acting strip elements can be brought into releasable contact with each other by means of projections on one of the strips being forced through holes in the other strip. By cutting the web at the lines of intended separation, separate closed garments are then formed. Although said method has advantages, the method implies that the absorbent article has the releasable surfaces of the co-acting strips lying in contact inside the garment which can provide a disadvantage when trying to open the garment.

Thus, the object of the invention is to provide a solution to the aforesaid problems by a particular method of producing a reclosable absorbent garment which can be manufactured by an in-line continuous process. The invention also seeks to provide a garment having a reclosable fastening arrangement which can be manufactured in an in-line continuous process.

SUMMARY OF THE INVENTION

The aforementioned object is solved by the method having the features defined in claim 1. Similarly, the garment of the invention is characterized by the features defined in claim 7.

Preferred embodiments of the invention are defined in the dependent claims.

In the claims, the term "releasably attachable" has been used to describe a material which is comprised in the first strip. It is to be understood that this term refers to a material which can be attached and re-attached to another part. For example such a material may be constituted by one part of a hook and loop material (such as the material sold under the trade name "VELCRO" for example). Other materials which allow attachment, removal and reattachment are also included within said term. Similarly, the term "reclosable fastening" also refers to a fastening comprising a releasably attachable material.

By means of the method and product of the invention, a single garment or a series of joined single garments is made available, which garment(s) are produced in the closed state (i.e. ready for being pulled on to the wearer as a normal pair of absorbent pants) in contrast to the open state in which normal nappies of the reclosable type are produced.

In a preferred embodiment of the invention, said garments are attached to one another after having been produced in an in-line process. By providing a line of weakening, such as a perforation or the like, between each of said garments, separation of individual garments or separation of a number of garments from the remainder is also possible. Such an embodiment allows the products to be supplied as a rolled up series of articles. Alternatively, with such an embodiment, said articles might be placed back-to-back in a joined stacked fashion. Such rolled-up or stacked joined articles have the additional advantage that said articles remain together, even when the outer packaging is removed. This joined relationship helps to prevent single absorbent articles becoming separated from a group of articles which can lead to the article becoming untidy or badly deformed (e.g. in a carrying bag or the like) as otherwise often occurs.

BRIEF DESCRIPTION OF THE DRAWINGS

The invention will now be described in more detail with reference to the accompanying drawings, in which.

DETAILED DESCRIPTION OF A PREFERRED EMBODIMENT

Figure 1:
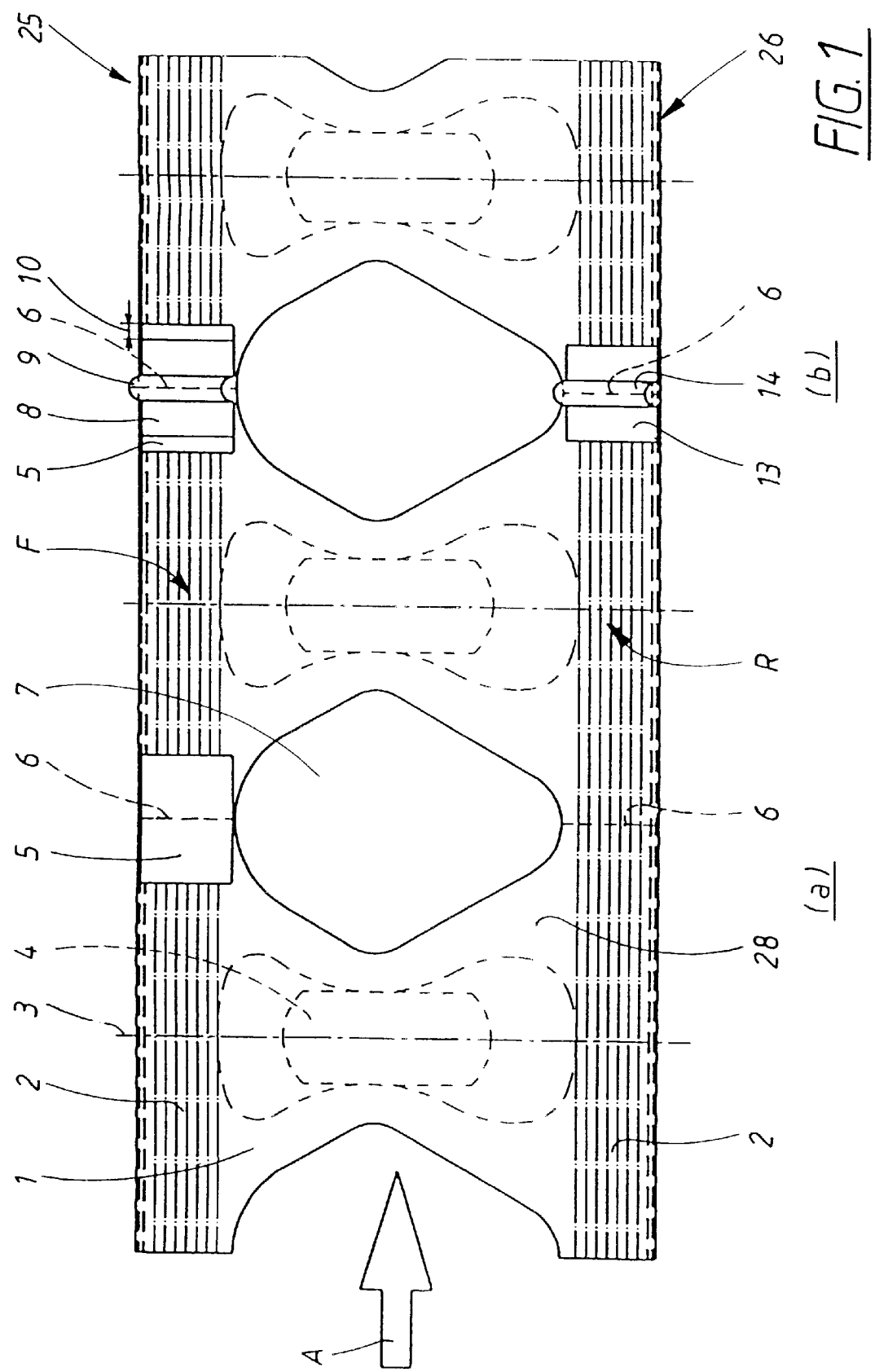
FIG. 1 shows the first stage of the method according to a preferred embodiment of the invention, wherein a web of attached absorbent garments is moved in the direction of arrow A through two first zones "(a)" and "(b)"

FIG. 1 shows a portion of a web 1 comprising a plurality of open absorbent articles laid side-by-side in connected fashion on a substantially flat conveying surface (not shown). The absorbent articles are delimited from one another in the shown embodiment by lines of weakening such as perforation lines 6. The web 1 thus-formed is therefore substantially continuous, apart from said lines of weakening which run substantially perpendicular to the two longitudinal edges 25, 26 of said web. In the present case, two lines of weakening 6 are provided between adjacent articles, one on either side of a cut-away portion 7 which is used to form the leg openings of the garments to be formed.

The denotations "F" and "R" in the figure are used to indicate the front and rear surfaces respectively of the final garment to be obtained.

The lines of weakening 6 thus form lines of intended separation (i.e. for later separation) between the articles. The separation process will be explained below.

Each absorbent article comprises an elasticated, or non-elasticated, waistband portion 2 at either longitudinal edge of the web 1, said waistband portions being spanned by one or more sheets 28 such as for instance an impervious back sheet and a pervious top sheet or liner. An absorbent core 4; or an absorbent layer, is maintained in some manner between the two waistband portions, substantially symmetrically with respect to the centreline 3 of each article Such an arrangement and the type of materials used will not be described in further detail since many types of such arrangement and materials are known to the skilled man.

Where an elasticated waistband is used, the line 6 (e.g. a perforation line) can be arranged so as not to sever the elastic threads of the waistband, which helps to give more structural integrity to the web during transport thereof in said production machine.

The web 1 is fed, preferably continuously in an in-line process, in the direction of arrow A, towards a zone "(a)". In zone "(a)", where in this embodiment a first preferred process step is carried out, a strip 5 of flexible material is attached to the web 1, for example by adhesive or ultrasound welding at the front F or rear R side, depending on which side (F or R) the stationary part of the releasable attachment closure is to be positioned. The strip 5, in the embodiment depicted, is thus applied over the line of intended separation 6 at the longitudinal edge 25, preferably with half the strip on one side and half on the other side of said line 6. The strip 5 comprises one of the elements of a releasable attachment means, such as for example the loop elements of a hook and loop attachment means. The loop elements may of course be formed integrally with said strip 5 or may be attached thereto.

The strip 5 will be applied to the outer surface of the sheet 28/waistband 2 with the loop elements facing away from the sheet 28 (i.e. out of the page in FIG. 1) The application of strip 5 is however only required when the reclosable element of strip 8 (to be described) cannot releasably adhere by itself to the surface to which strip 5 has been applied. Thus, if the waistband surface under strip 5 comprised e.g. nonwoven material, a suitable hook attachment means could be used (on strip 8) to releasably attach to this, such that strip 5 would not be required.

In order that the strip 8 can be releasably attached to strip 5 or the underlying surface in a reliable manner, said strip or surface should be relatively flat. Thus, in the depicted example using an elasticated waistband which comprises elastic elements adhered to said waistband region, it may be appropriate not to adhere the elastic elements to the waistband in the region where strip 8 would be attached. In this way elastic contraction forces are not applied in that region which will help to prevent the region from crinkling. Crinkling should of course be avoided since this would reduce the effective surface area of releasable connection.

The strip 5 is preferably provided itself with a line of weakening positioned directly above the line of intended separation 6. The line of weakening (e.g. perforation) can be made, or formed, on the strip 5 either before its placement over line 6 or can be produced together with line 6 (e.g. by perforating the web through strip 5). As a still further alternative, the line of weakening may be arranged in strip 5 after its application over a web 1 already provided with a line of weakening 6 in the waistband portion 2.

In zone "(b)", a flexible first strip 8 comprising the other element of the releasable attachment means is applied onto the strip 5, substantially symmetrically thereto. For example, if strip 5 comprises loop elements then strip 8 would comprise hook elements. Strip 8 is applied with the hook elements facing the loop elements of strip 5 such that the strip 8 is held releasably in position.

Strip 8 should preferably be of a soft, yet strong material, such as nonwoven material, on which the releasably attachable element has been fixedly attached.

Since the material of strip 8 will generally not be elasticated, the method of the invention (as will be described later) will in such a case require that a surplus 9 of material be available, said surplus being positioned directly above the line 6. As is shown in FIG. 1, this results in a gap being present beneath the surplus 9 of material of the strip 8 between the innermost attachment locations of the strip 8 to the strip 5. Said gap is shorter in length than the length of surplus material 9 (as seen in the longitudinal direction of said web 1). In the present case, the strip 8 has been chosen to be approximately equal to the length of strip 5. The surplus of material above line 6 is thus achieved by leaving a margin 10 at the outer edges of strip 8 with respect to strip 5.

A second strip 13 of flexible material, such as a soft and strong nonwoven material, is fixedly attached by means of an ultrasound weld 20 (see FIG. 4), or the like, at the opposite longitudinal edge 26 of the web 1 and on the same face of the web as strips 5 and 8. The strip 13 is applied in a similar manner to strip 8, such that a surplus of material 14 is left above line 6. As with strip 8, the gap between the attachment locations of strip 13 is shorter than the length of the surplus material 14 (as seen in the longitudinal direction of said web).

Figure 2:
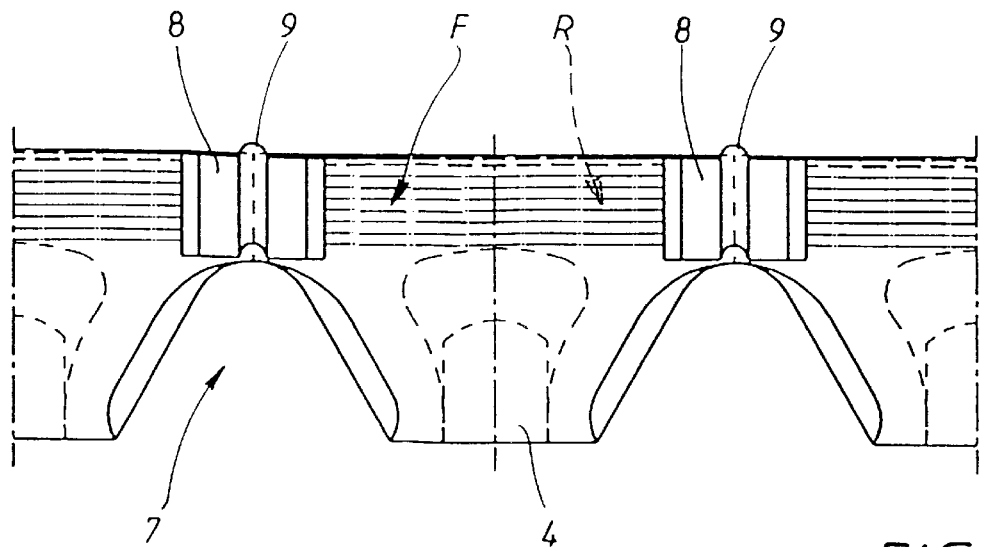
FIG. 2 shows a further stage of the production method, in which the web shown in FIG. 1 has been folded about a central longitudinal axis so that the front and rear parts of said article are moved into contact.

In a next step after zone "(b)" as shown in FIG. 2, the web 1 is folded longitudinally approximately midway between the longitudinal edges 25 and 26. The front and rear waistband portions are thereby placed together such that a row of connected articles is formed. At this stage, there is however no attachment between the front and rear surfaces F, R along the waistband.

Figure 3:
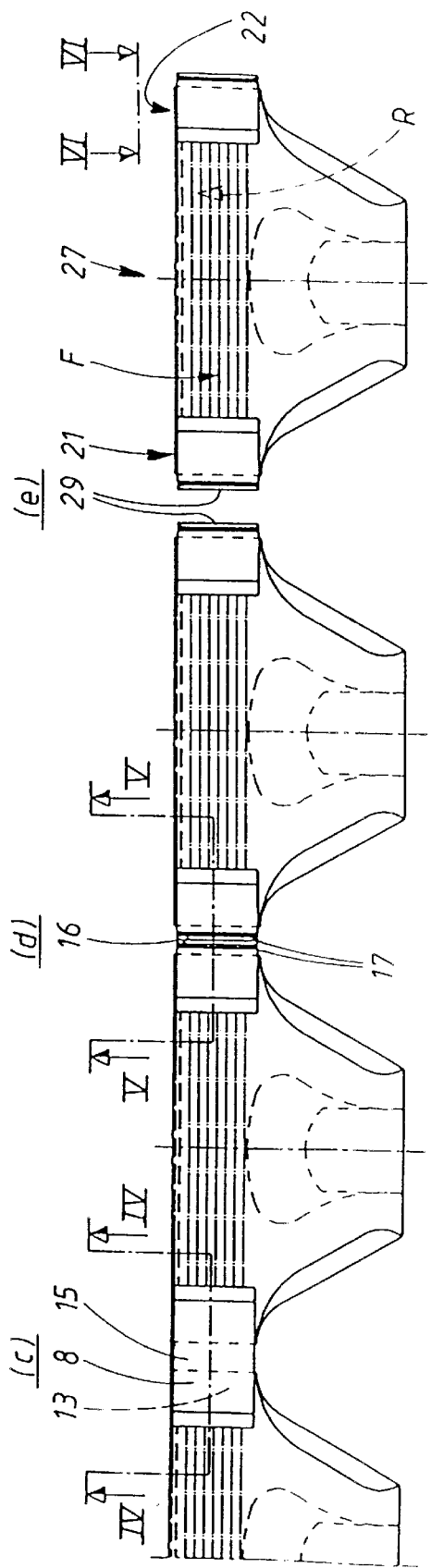
FIG. 3 shows a still further stage of said method of production, in which the series of interconnected absorbent articles are separated, welded and severed into a plurality of separate absorbent garments in the further zones "(c)", "(d)" and "(e)" respectively.

Moving from left to right, as seen with regard to FIG. 3, the folded web moves through zones "(c)", "(d)" and "(e)".

In zone "(c)", adjacent articles are longitudinally separated with respect to one another. The magnitude of said longitudinal separation is such that the line of intended separation 6 is severed on both front and rear surfaces, yet the first and second strips 8 and 13 remain intact, since they are not subject to any excessive tension due to the surplus of material which was provided. The material strip 5 (where this is provided) however, is severed across its line of separation.

When viewing the cross-section of zone "(c)" along line IV—IV it will be clear that between the strips 8 and 13, and between the inner edges of web 1 where the line 6 was placed, a free zone 15 of non-attachment is provided. It should also be noted that although FIG. 4 depicts the strip 8 as separated from the optional third strip 5, this is merely for clarity and the strip 8 would normally be attached to strip 5.

Having longitudinally separated the articles in zone "(c)" the folded web moves to zone "(d)" in which two welds 17, or other means for providing a secure attachment, are made across the free zone 15 so that the strips 8 and 13 are securely joined together. In a further embodiment (not shown) the two welds can be combined as a single weld.

Figure 5:
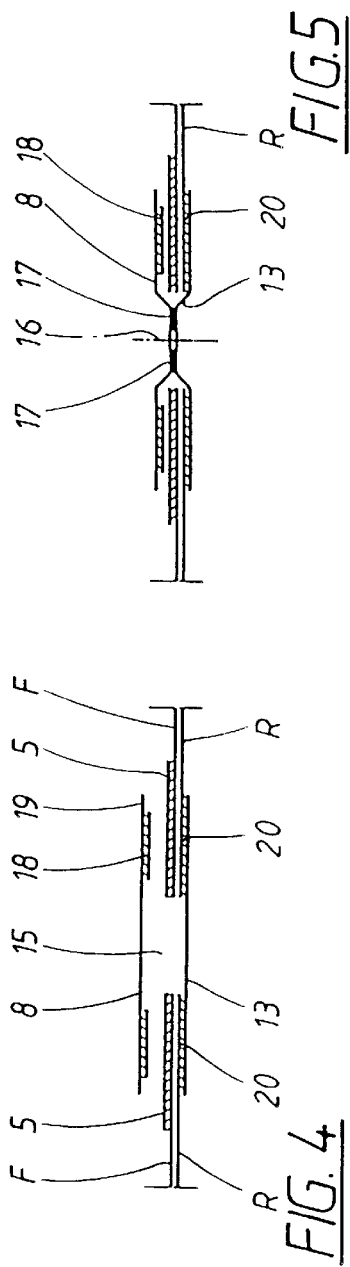
FIG. 5 shows a cross-sectional view through FIG. 3, on to line V—V in zone "(d)"

FIG. 5 shows a cross-sectional view through zone "(d)", whereby the position and extent of the two welds is shown. Although the releasable attachment portion 18 of strip 8 is not shown in contact with the underlying web 1 or the other part of the releasable attachment means, this will of course be the case. The strips have been shown as separate, merely for reasons of clarity. At this stage, the web will comprise a series of adjacent absorbent garments, separated by the welds 17.

Figure 4:
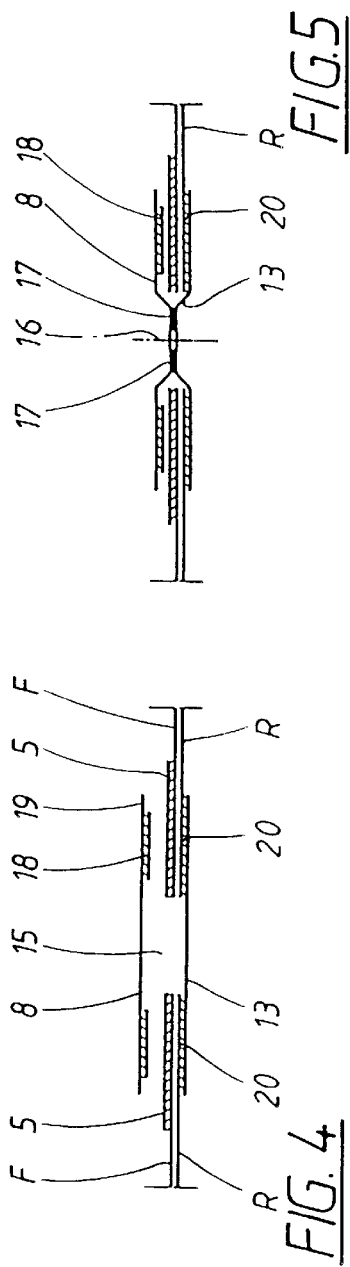
FIG. 4 shows a cross-sectional view through FIG. 3, on to line IV—IV in zone "(c)", however with the first strip raised away from the third strip attachment elements merely for reasons of clarity.

It should be noted that the relative dimensions of the parts shown in FIGS. 4 and 5 depict approximate relative size relationships, suitable for carrying out the invention.

In zone "(d)", a line 16 is also depicted. The line 16 depicts a line of severing or, in another embodiment, a line of intended severing. Taking the embodiment depicted in FIG. 3, the line 16 is a cut which passes through the strips 8 and 13 between, or through, the welds 17. Any elastic cords from the elasticated waistband present at this location will also be severed by said cut.

The web is then moved further to station "(e)", in which the articles are separated from one another by longitudinal displacement, such that the cut line 16 leaves opposing free edges 29 on adjacent articles 27. Each opposing free edge 29 will comprise the free ends of each of the strips 8 and 13 which will be flush with each other where the line 16 was made.

The produced separate article(s) 27 will thus have two reclosable fastening arrangements 21, 22 thereon, one on either side. Thus, it will be seen that by providing a reclosable fastening arrangement in the way described, separate articles or a series of closed separate articles can be simply packed into an outer packaging wrapper. On reaching the end user, the article(s) merely needs to be withdrawn from the packaging and put on like a pair of ordinary underpants, without any need to try and assemble the garment first. Once the garment is on the user, either side can be adjusted separately if desired by using the reclosing arrangement now provided In a further embodiment, the line of severance 16 can be replaced by a line of weakening, such that the products are held together as a strip, but with the possibility of the end user detaching one or more of said garments by an easy tearing action. With such an embodiment, the web of articles can be packed as a roll or as a zig-zag stack.

Figure 6:
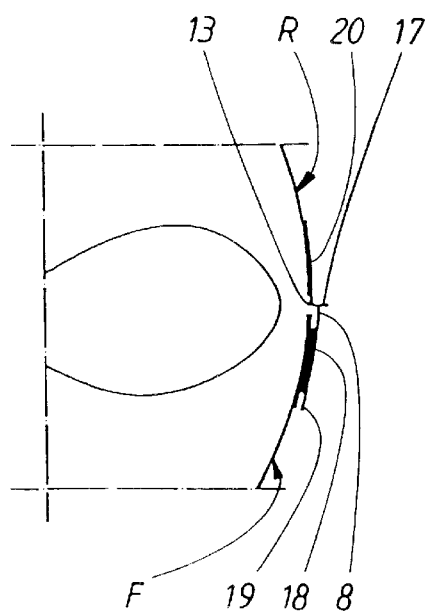
FIG. 6 shows a cross-sectional view, through one portion of the closed separate garment shown in FIG. 3 after zone "(e)", on to line VI—VI.
Figure 7:
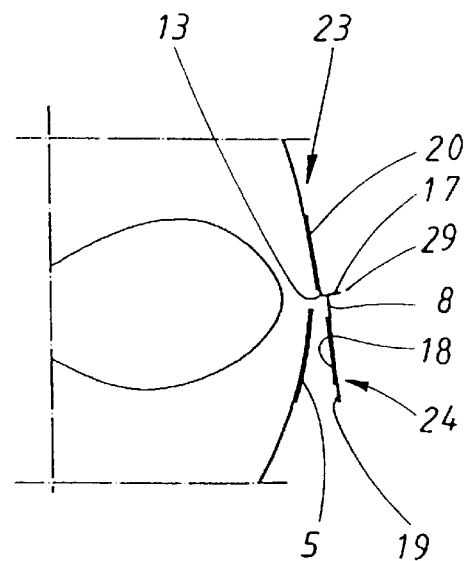
FIG. 7 shows a cross-sectional view similar to FIG. 6, wherein the reclosable fastening means has been opened.

FIG. 6 shows a view through one side of the absorbent garment of FIG. 3, after separation at zone "(e)" and in the closed state, however expanded out as if a user was wearing the garment, so that the cut-out portion 7 represents a leg opening FIG. 7 shows the same view as FIG. 6 but in the opened state, ready for removal or adjustment.

As will be seen, the front F and rear R sections meet a short distance away from each other although adjustment by opening and reclosing will allow them to overlap. A first part of the reclosable fastening arrangement 22 is attached to the rear section R and comprises said second strip 13 securely attached to the outer surface thereof by means of connection 20 (see FIG. 4). Attached to said second strip 13 by means of weld 17 is said first strip 8. Said first strip 8 comprises one half of the releasable attachment means 18. Numeral 19 denotes a free forward edge portion which is left so that the strip end can be gripped. Said first part is thus a combined strip having first and second ends 23 and 24 respectively, one of said ends being permanently attached and the other being releasably attachable to the front section at 5.

As will be seen however, at the middle of the combined strip, the two strips 8 and 13 are securely attached together so that their ends lie flush with one another at free outer tab 29, due to the cutting procedure adopted. By this unique arrangement of the strips so as to be flush with one another (and thus providing a free outer tab) at the joining portion, as opposed to the traditional overlapping connection which is used for reclosable strips, a novel garment is arrived at which allows in-line production of the same so as to produce a closed garment directly from the production line, without further intervention by machine or personnel.

The further particular features of the garments having fastening arrangements in accordance with the present invention will be apparent to the skilled man in particular from viewing FIGS. 6 and 7.

It should be understood that the references to "front" and "rear" sections (F and R) of the article are not limiting for the position of the reclosable means. Thus, the references "F" and "R" respectively in FIG. 6 could alternatively have been "R" and "F" respectively, such that the strip 13 would instead be attached to the front section F and not the rear section R as shown.

The function of releasing, re-attaching and adjusting of the fastening arrangements 21 and 22 will be clear to the skilled man and thus need not be described in further detail here.

The aforegoing description merely contains illustrative examples of how the invention may be carried out. The invention may however be varied in many ways without departing from the scope thereof as defined by the appended claims. For example, although it has been described that surplus material 9 is left over line 6 for strips 8 and 13, in order that said strips will not break when the separation of zone "(c)" is carried out, the strips could be arranged to be elastic in said region instead and be laid relatively flat over said line 6. However, such an embodiment is not preferred.

A further variant of the invention may also be that strips 5 and 8, or the waistband 2 and the strip 8 (if no strip 5 is present), are each provided with one half of a male/female coupling. One half (e.g. the male part) of the coupling would be fixed in position on the strip 8 and one half (e.g. the female part) would be fixed in position on strip 5 (or waistband 2, if no strip 5 is present). Such male and female connections could be moulded or otherwise attached or even formed together with the strip. This arrangement would allow the reclosure of the article to a fixed position each time that the article is opened and reclosed. As an example of how this would appear, in FIG. 7, the parts 18 and 5 could be a male part and a female part respectively.

Further embodiments and modifications of the invention within the scope of the appended claims will be apparent to the skilled man.

What is claimed is:

1. Method of producing reclosable absorbent garments for the absorption of human exudate, from a web comprising a plurality of open absorbent articles attached side-by-side so as to form a substantially continuous web of attached articles having opposed longitudinal edges, and wherein a line of intended separation is arranged between adjacent articles, said method comprising the steps of:
    a) applying a first strip of flexible material across the line of intended separation (6) at one longitudinal edge of the web, said first strip comprising a zone of releasably attachable material facing said web and positioned on either side of said line,
    b) applying a second strip of flexible material across the line of intended separation at the other longitudinal edge of the web,
    c) folding the web between the longitudinal edges (25, 26) so as to obtain a web of articles folded front side to rear side,
    d) longitudinally separating said adjacent articles at said line of intended separation but without rupturing said strips, so as to provide a free zone between said strips and the adjacent separated edges of each article,
    (e) securely joining said first and second strips together across said free zone so as to form closed garments.

2. Method according to claim 1 wherein, prior to step (a), a third strip of flexible material is applied to said web across the line of intended separation at the same longitudinal edge to which said first strip is to be attached, and wherein said third strip comprises material to which the releasably attachable material of said first strip will attach.

3. Method according to claim 1, wherein said first and second strips are attached to said web at attachment locations on either side of the line of intended separation so as to leave a gap extending on either side of said line of intended separation so as to leave a gap extending on either side of said line of intended separation, and wherein the length of material of said strips between said attachment locations is greater than the length of the gap.

4. Method according to claim 1, wherein said absorbent garments are separated completely from one another by severing the joined strips at a location intermediate of where said strips have been joined together, thus producing a series of separated, closed absorbent garments.

5. Method according to claim 2, wherein said third strip is provided with a perforation line which is positioned in line with said line of intended separation.

6. Method according to claim 1, wherein each of said garments has an elasticated waistband, the elastication means for said waistband being applied by adhesion prior to the application of any of said strips, and wherein, in the region where said strips are to be attached, said waistband is not adhered to said web, to thus provide a relatively flat outer surface at said region.

7. Absorbent garment for the absorption of human exudate, said absorbent garment comprising a waistband portion divided into front and rear sections by means of two reclosable fastening arrangements, each of which fastening arrangements is positioned at a respective end of said front and rear sections, wherein each of said fastening arrangements comprises first and second ends, the first end being fixedly secured to said front or rear section and the second end comprising a reclosable fastening portion, the first end and the second end each being provided on respective first and second separate strips, each of the first and second strips having a respective inner surface facing the absorbent garment and a respective outer end, wherein the inner surface of the outer end of one strip of said strips is fixedly secured to the inner surface of the outer end of the other strip of said strips so that the outer two ends are flush with each other in order to provide a combined strip having a free outer tab containing the two flush ends.

8. Reclosable absorbent garment according to claim 7, wherein said waistband portion comprises one or more elastic elements adhered thereto, and in that a zone of non-adhesion of said elastic elements is provided on said waistband beneath said reclosable fastening arrangements, such that said waistband is substantially flat in said zone compared to the rest of said elasticated waistband.

9. Reclosable garment according to claim 7, wherein said absorbent garment is a closed pair of absorbent reclosable pants comprising an absorbent core.

10. Reclosable garment according to claim 7, wherein said reclosable portion on said first strip is one part of a male/female coupling, and in that said waistband, or optional third strip thereon, is provided with the other part of said male/female coupling.

* * * * *